United States Patent
Lamka

(10) Patent No.: US 8,267,694 B1
(45) Date of Patent: Sep. 18, 2012

(54) HEALTH AND FITNESS SYSTEMS

(76) Inventor: Anthony J. Lamka, Phoenix, AZ (US)

( * ) Notice: Subject to any disclaimer, the term of this patent is extended or adjusted under 35 U.S.C. 154(b) by 382 days.

(21) Appl. No.: 12/493,090

(22) Filed: Jun. 26, 2009

Related U.S. Application Data

(60) Provisional application No. 61/076,580, filed on Jun. 27, 2008, provisional application No. 61/102,611, filed on Oct. 3, 2008.

(51) Int. Cl.
*G09B 19/00* (2006.01)

(52) U.S. Cl. ........................................ 434/236

(58) Field of Classification Search .................. 434/156, 434/188, 236, 262, 276, 433, 247
See application file for complete search history.

(56) References Cited

U.S. PATENT DOCUMENTS

| | | | |
|---|---|---|---|
| 5,542,420 A | 8/1996 | Goldman et al. | |
| 5,888,172 A * | 3/1999 | Andrus et al. | 482/7 |
| 5,890,128 A | 3/1999 | Diaz et al. | |
| 6,368,272 B1 | 4/2002 | Porumbescu | |
| 6,749,432 B2 | 6/2004 | French et al. | |
| 6,814,579 B2 * | 11/2004 | Bent | 434/433 |
| 6,991,465 B2 * | 1/2006 | Matthews | 434/260 |
| 7,024,369 B1 | 4/2006 | Brown et al. | |
| 7,281,928 B1 * | 10/2007 | Freeman | 434/156 |
| 2003/0207237 A1 * | 11/2003 | Glezerman | 434/118 |
| 2004/0009462 A1 * | 1/2004 | McElwrath | 434/350 |
| 2004/0018474 A1 | 1/2004 | D'Ippolito | |
| 2004/0048231 A1 * | 3/2004 | Perlin | 434/263 |
| 2004/0072130 A1 * | 4/2004 | Safran, Sr. | 434/169 |
| 2005/0130113 A1 * | 6/2005 | Bergan | 434/350 |
| 2005/0154609 A1 * | 7/2005 | Kurtz | 705/1 |
| 2005/0260547 A1 * | 11/2005 | Moody | 434/176 |
| 2006/0025282 A1 | 2/2006 | Redmann | |
| 2006/0029921 A1 * | 2/2006 | Walther et al. | 434/382 |
| 2007/0009879 A1 * | 1/2007 | Kentof | 434/365 |
| 2007/0219809 A1 * | 9/2007 | Peyton | 705/1 |
| 2008/0027673 A1 * | 1/2008 | Trumm | 702/160 |
| 2008/0085503 A1 * | 4/2008 | Handzel | 434/369 |
| 2008/0124690 A1 * | 5/2008 | Redlich | 434/236 |
| 2008/0145826 A1 * | 6/2008 | Cohen et al. | 434/262 |
| 2008/0147502 A1 | 6/2008 | Baker | |
| 2008/0254420 A1 * | 10/2008 | Nerenberg | 434/236 |
| 2009/0023118 A1 * | 1/2009 | Janes | 434/129 |
| 2009/0298039 A1 * | 12/2009 | Glazier | 434/362 |

FOREIGN PATENT DOCUMENTS

| | | |
|---|---|---|
| GB | 2398135 A | 8/2004 |
| WO | WO2007134376 A1 | 11/2007 |

OTHER PUBLICATIONS

Julie Sturgeon, Janice Meer, "The First Fifty Years 1956-2006 The President's Council on Physical Fitness and Sports Revisits its Roots and Charts its Future", http://www.fitness.gov/50thanniversary/The%20First%20Fifty%20Years.pdf, date of publication unknown, 24 pages, Internet.
http://www.fitnessbeginnings.com/exercise-videos.html, Fitness Beginnings Fitness Videos for Kids, date of publication unknown, 8 pages, Internet.
Anthony J. Lamka; U.S. Trademark Registration No. 3,741,681, registered on Jan. 26, 2010.
Anthony J. Lamka; U.S. Trademark Registration No. 3,751,166, "Operation Tone-Up", registered on Feb. 23, 2010.
Anthony J. Lamka; U.S. Trademark Registration No. 3,743,712, "Mr. Tone", registered on Feb. 2, 2010.

* cited by examiner

*Primary Examiner* — Kurt Fernstrom
(74) *Attorney, Agent, or Firm* — Snell & Wilmer, LLP

(57) ABSTRACT

Systems and methods integrating childhood health and fitness into educational programs. Included are integrating multimedia entertainment concepts into health and fitness educational programs that are combined with multiple curricula.

24 Claims, 9 Drawing Sheets

FIG. 6

HEALTH AND FITNESS SYSTEMS

CROSS-REFERENCE TO RELATED APPLICATION

The present application is related to and claims priority from prior provisional application Ser. No. 61/102,611, filed Oct. 3, 2008, entitled "HEALTH AND FITNESS SYSTEMS"; and, this application is related to and claims priority from prior provisional application Ser. No. 61/076,580, filed Jun. 27, 2008, entitled "HEALTH AND FITNESS SYSTEMS", the contents of both of which are incorporated herein by this reference and are not admitted to be prior art with respect to the present invention by the mention in this cross-reference section.

BACKGROUND

This invention relates to providing a system for improved childhood health and fitness. More particularly, this invention relates to providing and integrating health and fitness systems into educational programs. Further, this invention relates to providing systems for integrating multimedia entertainment concepts into individual, and group, health and fitness educational programs. Presently, systems for childhood health and fitness lack health and fitness educational programs that integrate into core curricula while using multimedia entertainment to enhance learning. Thus, a need exists for an improved system of health and fitness educational programs, with integrated curricula, utilizing multimedia entertainment to enhance learning.

OBJECTS AND FEATURES OF THE INVENTION

A primary object and feature of the present invention is to provide systems for supplying the above-mentioned improvements.

It is a further object and feature of the present invention to provide systems for improved childhood health and fitness.

It is a further object and feature of the present invention to provide systems for integrating health and fitness systems into educational programs.

It is a further object and feature of the present invention to provide systems for integrating multimedia entertainment concepts into individual, and group, health and fitness educational programs.

It is a further object and feature of the present invention to provide systems for providing characters and story plots providing integrating multimedia entertainment concepts into health and fitness educational programs, which further integrate into broader educational curricula.

It is a further object and feature of the present invention to provide systems for monetizing methods utilizing story plots relating to one or more characters related to one or more food groups, while integrating multimedia entertainment concepts into health and fitness educational programs.

It is a further object and feature of the present invention to provide systems for monetizing methods utilizing story plots relating to one or more characters related to one or more food groups, and one or more characters related to one or more exercise routine, and while integrating multimedia entertainment concepts into health and fitness educational programs.

A further primary object and feature of the present invention is to provide such a system that is efficient, inexpensive, and handy. Other objects and features of this invention will become apparent with reference to the following descriptions.

SUMMARY OF THE INVENTION

In accordance with a preferred embodiment hereof, this invention provides a system relating to benefiting children comprising: at least one cartoon character structured and arranged to promote educational interest of such children; and education materials relating to nutritional health of such children; wherein such education materials relate to such at least one cartoon character; and wherein such education materials comprise a plurality of educational curricula; and at least one educational materials promoter structured and arranged to promote use of such education materials to benefit of such children.

Moreover, it provides such a system wherein such plurality of educational curricula comprises at least mathematics. Additionally, it provides such a system wherein such plurality of educational curricula comprises at least science. Also, it provides such a system wherein such plurality of educational curricula comprises at least reading and writing. In addition, it provides such a system wherein such plurality of educational curricula comprises at least three of the group consisting essentially of: mathematics; science; reading; writing; physical education.

And, it provides such a system further comprising at least one competition structured and arranged to promote participatory interest of children. Further, it provides such a system further comprising at least one prize related to such at least one competition. Even further, it provides such a system wherein such at least one prize comprises at least one monetary prize. Moreover, it provides such a system wherein such at least one prize comprises at least one voucher. Additionally, it provides such a system wherein such at least one prize comprises at least one hand-held electronic device.

Also, it provides such a system wherein such at least one prize comprises at least one computer system. In addition, it provides such a system wherein such at least one prize comprises at least one multimedia prize. And, it provides such a system wherein such at least one competition is sponsored by at least one sponsor. Further, it provides such a system further comprising at least one personal appearance of such at least one cartoon character. Even further, it provides such a system wherein such at least one cartoon character represents at least one nutritional element.

Moreover, it provides such a system wherein such at least one cartoon character represents at least water. Additionally, it provides such a system wherein such at least one cartoon character represents at least protein. Also, it provides such a system wherein such at least one cartoon character represents at least carbohydrates. In addition, it provides such a system wherein such at least one cartoon character represents at least minerals. And, it provides such a system wherein such at least one cartoon character represents at least vitamins. Further, it provides such a system wherein such at least one cartoon character represents at least fats.

Even further, it provides such a system wherein such at least one cartoon character represents at least sodium. Moreover, it provides such a system wherein such at least one cartoon character represents at least sugars. Additionally, it provides such a system wherein such education materials comprise at least one exercise cycle. Also, it provides such a system wherein such at least one exercise cycle comprises at least one multimedia disc. In addition, it provides such a system wherein such at least one multimedia disc comprises at least one DVD. And, it provides such a system wherein such at least one multimedia disc comprises at least one CD. Further, it provides such a system further comprising at least one web site providing such educational materials.

In accordance with another preferred embodiment hereof, this invention provides a method relating to benefiting children comprising the steps of: providing a plurality of cartoon characters structured and arranged to promote educational interest of children; and providing education materials; wherein such education materials relate to nutritional health of such children; wherein such education materials relate to such plurality of cartoon characters; wherein such plurality of cartoon characters each represent at least one nutritional element; wherein such plurality of represented nutritional elements comprises at least water, protein, carbohydrates, minerals, vitamins, fats, sodium, and sugars; wherein such education materials relate to a plurality of educational curricula; and wherein such plurality of educational curricula comprises at least three of the group consisting essentially of mathematics, science, reading, writing, physical education; and promoting use of such education materials to benefit of such children.

In accordance with another preferred embodiment hereof, this invention provides a method relating to benefiting children comprising the steps of: providing at least one cartoon character structured and arranged to promote educational interest of children; and providing education materials; wherein such education materials relate to nutritional health of such children; wherein such education materials relate to such at least one cartoon character; and wherein such education materials relate to a plurality of educational curricula; and promoting use of such education materials to benefit of such children.

Even further, it provides such a method wherein such plurality of educational curricula comprises at least mathematics. Moreover, it provides such a method wherein such plurality of educational curricula comprises at least science. Additionally, it provides such a method wherein such plurality of educational curricula comprises at least reading and writing. Also, it provides such a method wherein such plurality of educational curricula comprises at least three of the group consisting essentially of: mathematics; science; reading; writing; physical education.

In addition, it provides such a method further comprising the step of marketing such at least one cartoon character. And, it provides such a method further comprising the step of promoting at least one competition structured and arranged to promote participatory interest of children. Further, it provides such a method further comprising the step of providing at least one prize related to such at least one competition. Even further, it provides such a method wherein such at least one prize comprises at least one monetary prize. Moreover, it provides such a method wherein such at least one prize comprises at least one voucher. Additionally, it provides such a method wherein such at least one prize comprises at least one hand-held electronic device. Also, it provides such a method wherein such at least one prize comprises at least one computer system.

In addition, it provides such a method wherein such at least one prize comprises at least one multimedia prize. And, it provides such a method further comprising the step of obtaining at least one sponsor. Further, it provides such a method further comprising the step of providing at least one personal appearance of such at least one cartoon character. Even further, it provides such a method wherein such at least one cartoon character represents at least one nutritional element.

Even further, it provides such a method wherein such at least one cartoon character represents at least water. Even further, it provides such a method wherein such at least one cartoon character represents at least protein. Even further, it provides such a method wherein such at least one cartoon character represents at least carbohydrates. Even further, it provides such a method wherein such at least one cartoon character represents at least minerals. Even further, it provides such a method wherein such at least one cartoon character represents at least vitamins. Even further, it provides such a method wherein such at least one cartoon character represents at least fats. Even further, it provides such a method wherein such at least one cartoon character represents at least sodium. Even further, it provides such a method wherein such at least one cartoon character represents at least sugars.

Even further, it provides such a method wherein use of such education materials to benefit of such children promotes at least one exercise cycle. Even further, it provides such a method further comprising the step of providing such at least one exercise cycle on at least one multimedia disc. Even further, it provides such a method wherein such at least one multimedia disc comprises at least one DVD. Even further, it provides such a method wherein such at least one multimedia disc comprises at least one CD. Even further, it provides such a method further comprising the step of providing at least one web site to obtain such educational materials. Even further, it provides such a method further comprising the step of assisting merchandizing such at least one cartoon character. Even further, it provides such a method further comprising the step of assisting fund-raising to support operational expenses. This invention also provides each and every novel feature, element, combination, step and/or method disclosed or suggested by this provisional patent application.

BRIEF DESCRIPTION OF THE DRAWINGS

FIG. 6 shows a schematic view, illustrating at least one weekly tracking form, according to the preferred embodiment of FIG. 3.

DETAILED DESCRIPTION OF THE BEST MODES AND PREFERRED EMBODIMENTS OF THE INVENTION

Figure 1:
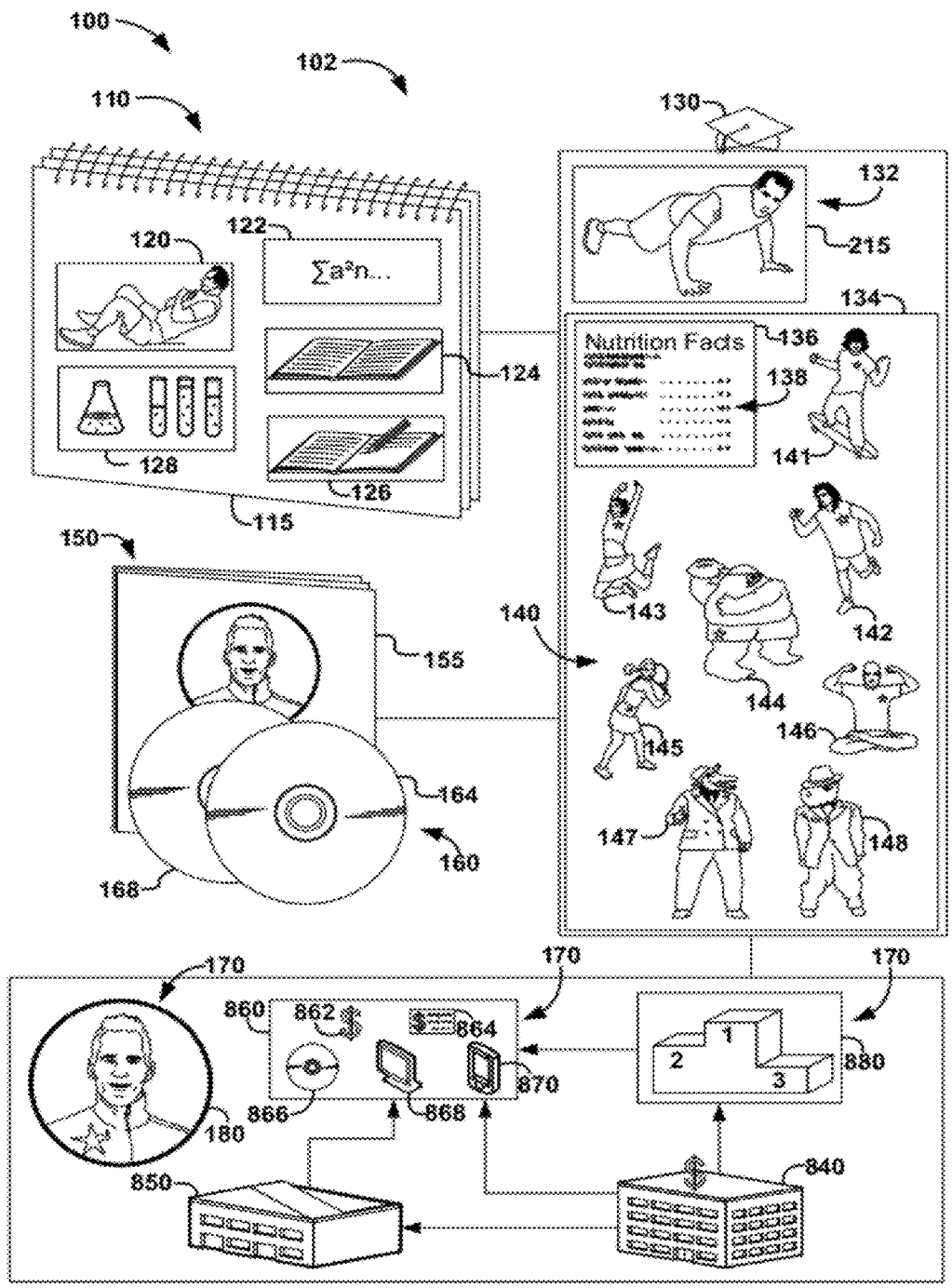
FIG. 1 shows a schematic view, illustrating a health and fitness system, according to a preferred embodiment of the present invention.

FIG. 1 shows a schematic view, illustrating at least one health and fitness program 102 of health and fitness system 100, according to a preferred embodiment of the present invention. Health and fitness system 100 preferably comprises health and fitness program 102 preferably comprising health and fitness education 130, as shown. At least one integrated curriculum 110 preferably implements health and fitness education 130, preferably through at least one curriculum instruction manual 115, as shown. Upon reading this specification, those skilled in the art will appreciate that, under appropriate circumstances, considering such issues as future technology, cost, learning methods, etc., other curricula instruction media, such as, for example, CD, DVD, electronic files, etc., may suffice.

Curriculum instruction manual 115 (at least embodying herein education materials; and at least herein embodying wherein such education materials relate to a plurality of educational curricula) preferably comprises curriculum instruction, as shown, preferably relating to physical education 120, preferably mathematics 122 (at least herein embodying wherein such plurality of educational curricula comprises at least mathematics), preferably reading 124, preferably writing 126 (at least herein embodying wherein such plurality of educational curricula comprises at least reading and writing), and preferably science 128 (at least herein embodying wherein such plurality of educational curricula comprises at least science). This arrangement at least herein embodies wherein such plurality of educational curricula comprises at least three of the group consisting essentially of: mathematics; science; reading; writing; physical education. Upon reading this specification, those skilled in the art will appreciate that, under appropriate circumstances, considering such issues as future technology, cost, learning methods, etc., other curricula, such as, for example, history, home economics, social studies, etc., may suffice. In addition, health and fitness program 102 preferably comprises student materials 150, as shown. Student materials 150 preferably comprise at least one student manual 155 and preferably at least one multimedia disc 160, as shown. Such at least one multimedia disc 160 preferably comprises, as shown, at least one DVD 164 (at least herein embodying wherein such at least one multimedia disc comprises at least one DVD), alternately preferably at least one CD 168 (at least herein embodying wherein such at least one multimedia disc comprises at least one CD). Upon reading this specification, those skilled in the art will appreciate that, under appropriate circumstances, considering such issues as future technology, cost, multimedia recording methods, etc., other multimedia storage mediums, such as, for example, cassettes, memory cards, cartridges, handheld personal media devices, etc., may suffice.

Student materials 150 and curriculum instruction manual 115 preferably provide health and fitness education 130, preferably when used collectively, alternately preferably when used individually, to student 821 (this arrangement at least herein embodying wherein such education materials relate to nutritional health of such children). Health and fitness education 130 preferably instructs both in exercise technique 132 and preferably in nutrition understanding 134, as shown.

Exercise technique 132 preferably instructs student 821 preferably in both proper performance of at least one exercise 405 and preferably at least one exercise cycle 400. Instruction in exercise technique 132 preferably minimizes injuries from improper exercise and maximizes success of at least one student 821 (see FIG. 8) in completing heath and fitness program 102.

Learning nutrition understanding 134 preferably teaches about food-product nutrition information 136, as shown, preferably detailing each nutritional element 138 and preferably its physiological interaction. Using at least one nutrition-associated character 140, in health and fitness education 130 of health and fitness program 102, as shown, preferably enhances learning retention of nutrition understanding 134 (this arrangement at least herein embodying wherein such education materials relate to such at least one cartoon character).

Nutrition-associated character 140 preferably is associated with nutritional element 138 (this arrangement at least herein embodying wherein such at least one cartoon character represents at least one nutritional element). Nutrition-associated character 140 (at least herein embodying at least one cartoon character structured and arranged to promote educational interest of children) preferably comprises, as shown, at least one carbohydrate associated character 141 (at least herein embodying wherein such at least one cartoon character represents at least carbohydrates), preferably at least one protein associated character 142 (at least herein embodying wherein such at least one cartoon character represents at least protein), preferably at least one vitamin associated character 143 (at least herein embodying wherein such at least one cartoon character represents at least vitamins), preferably at least one mineral associated character 145 (at least herein embodying wherein such at least one cartoon character represents at least minerals), preferably at least one fat associated character 144 (at least herein embodying wherein such at least one cartoon character represents at least fats), preferably at least one water associated character 146 (at least herein embodying wherein such at least one cartoon character represents at least water), preferably at least one sodium associated character 147 (at least herein embodying wherein such at least one cartoon character represents at least sodium), and preferably at least one sugar associated character 148 (at least herein embodying wherein such at least one cartoon character represents at least sugars). Upon reading this specification, those skilled in the art will now appreciate that, under appropriate circumstances, considering such issues as then nutritional understanding, cost, etc., other nutritional element associations, such as, for example, combined associations, cholesterol associations, enzyme associations, smoking associations, etc., may suffice.

To increase participation of student 821, health and fitness program 102 preferably further comprises at least one motivational element 170, as shown. Such at least one motivational element 170 preferably may comprise, as shown, at least one motivational character 180, alternately preferably at least one prize 860, alternately preferably at least one competition 880. Upon reading this specification, those skilled in the art will now appreciate that, under appropriate circumstances, considering such issues as cost, sponsors, participant goals, etc., other motivational elements, such as, for example, group participation, self-awareness, etc., may suffice.

Motivational character 180 preferably inspires student 821, preferably through at least one motivational story, contained in student materials 150. In such at least one motivational story, a history of motivational character 180 learning health and fitness education 130 is preferably outlined. Motivational character 180 is preferably primarily associated with health and fitness. Further, motivational character 180 preferably "practices what is taught" in health and fitness education 130, thereby preferably teaching by example. Upon reading this specification, those skilled in the art will now appreciate that, under appropriate circumstances, considering such issues as target audience, marketing, costs, etc., other motivational characters may suffice.

Competition 880 preferably provides motivation to student 821. At least one measure of progress of student 821 is taken, preferably using at least one comparative record 277 (see FIG. 2). Competition 880 preferably ranks student 821, preferably throughout participation in health and fitness program 102, based on such at least one measure of progress. Rankings of student 821 are preferably available to student 821 to assist in motivating progress in student 821. Upon reading this specification, those skilled in the art will now appreciate that, under appropriate circumstances, considering such issues as cost, participating groups, etc., other competitions, such as, for example, day-event competitions, athletic events, participation activity counts, etc., may suffice.

Figure 8:
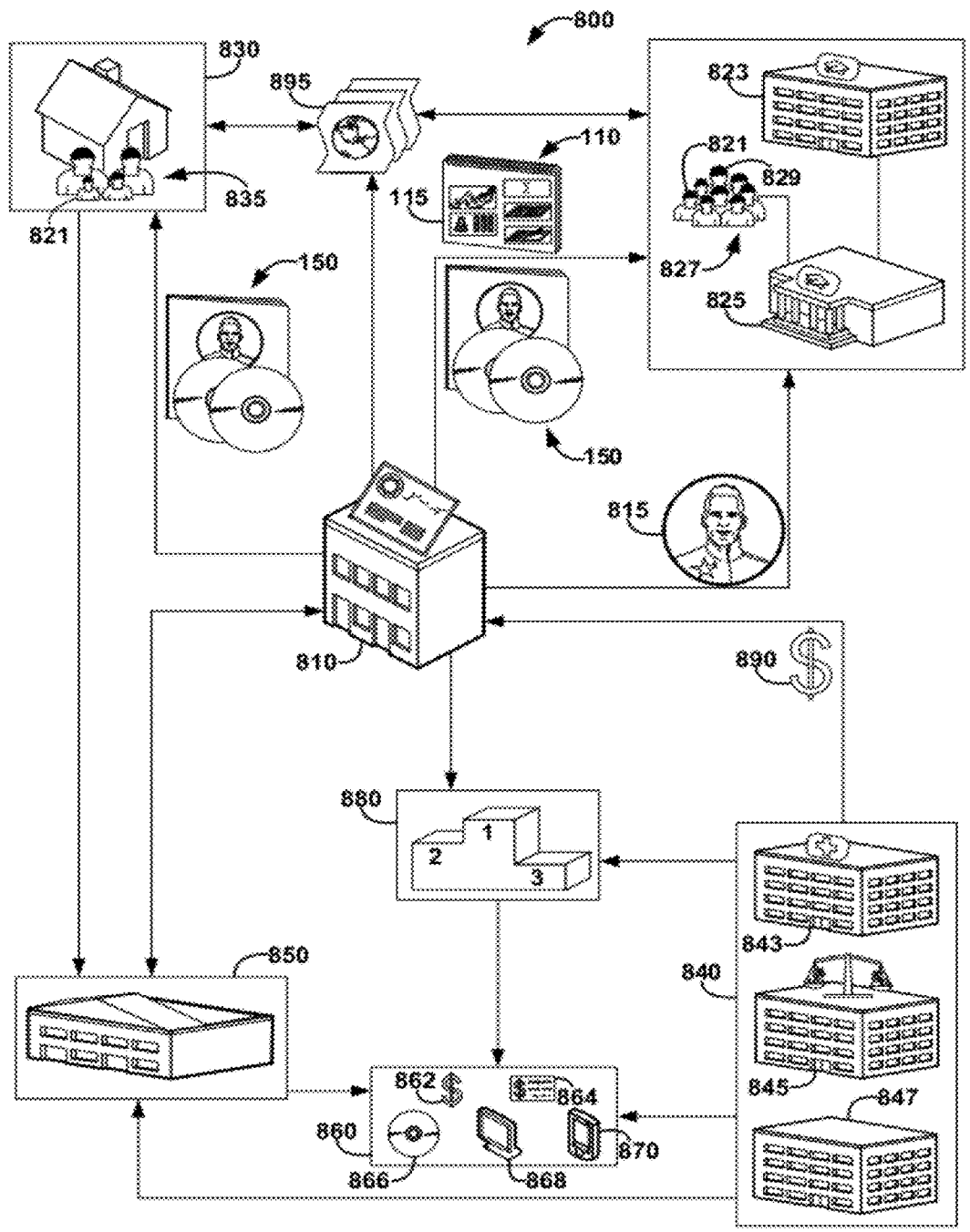
FIG. 8 shows a schematic view, illustrating at least one health and fitness method, according to the preferred embodiment of FIG. 4B.

Competition 880 preferably comprises individual competition, alternately preferably group competition. Competition 880, as shown in FIG. 8, in at least one school 825 of at least one school district 823 may preferably place student 821 in competition preferably between fellow classmates within at least one class 827, alternately preferably may place class 827, school 825 and/or school district 823 in competition with other classes 827, schools 825, and/or school districts 823 respectively. Outside of schools 825, such as in at least one home school 830, student 821 may preferably also participate in competition 880 preferably individually, alternately preferably with groups to which student 821 may belong. Upon reading this specification, those skilled in the art will now appreciate that, under appropriate circumstances, considering such issues as available groups, cost, participating user preference, etc., other competition groups, such as, for example, online social groups, community groups, religious groups, organizational groups, etc., may suffice.

Prizes 860 are preferably awarded to winners of competition 880. Additionally, prize 860 may preferably be awarded for completing portions of health and fitness system 100. Prize 860 may preferably comprise, as shown, at least one monetary prize 862 (at least herein embodying wherein such at least one prize comprises at least one monetary prize), alternately preferably at least one personal electronic device 870 (at least herein embodying wherein such at least one prize comprises at least one hand-held electronic device, e.g., PDA, MP3 player, handheld video game, etc.), alternately preferably at least one voucher 864 (at least herein embodying wherein such at least one prize comprises at least one voucher), alternately preferably at least one multimedia prize 866 (at least herein embodying wherein such at least one prize comprises at least one multimedia prize, e.g., movie, game, music, software, etc.), alternately preferably at least one computer 868 (at least herein embodying wherein such at least one prize comprises at least one computer system). Upon reading this specification, those skilled in the art will now appreciate that, under appropriate circumstances, considering such issues as future technology, user preference, etc., other prizes, such as, for example, toys, clothes, recognition, etc., may suffice.

Competitions 880 and prizes 860 are preferably provided by at least one sponsor 840 (see FIG. 8). Voucher 864, provided by sponsor 840, preferably provides at least one discount on goods and/or services, preferably associated to sponsor 840. Additionally, at least one partner 850 may also preferably provide prizes 860 (see FIG. 8).

Health and fitness program 102 preferably is implemented over at least one course of about eight weeks. Health and fitness program 102 preferably promotes exercising about three days per week, while also providing cognitive understanding throughout the period of implementation. Further, participation in heath and fitness program 102 preferably instills in student 821 habits that lead student 821 to continue following the principles taught in heath and fitness program 102. Upon reading this specification, those skilled in the art will now appreciate that, under appropriate circumstances, considering such issues as physical abilities of students, physical goals, costs, etc., other periods of implementation, such as, for example 10 weeks, six weeks, three months, etc., may suffice.

Figure 2:
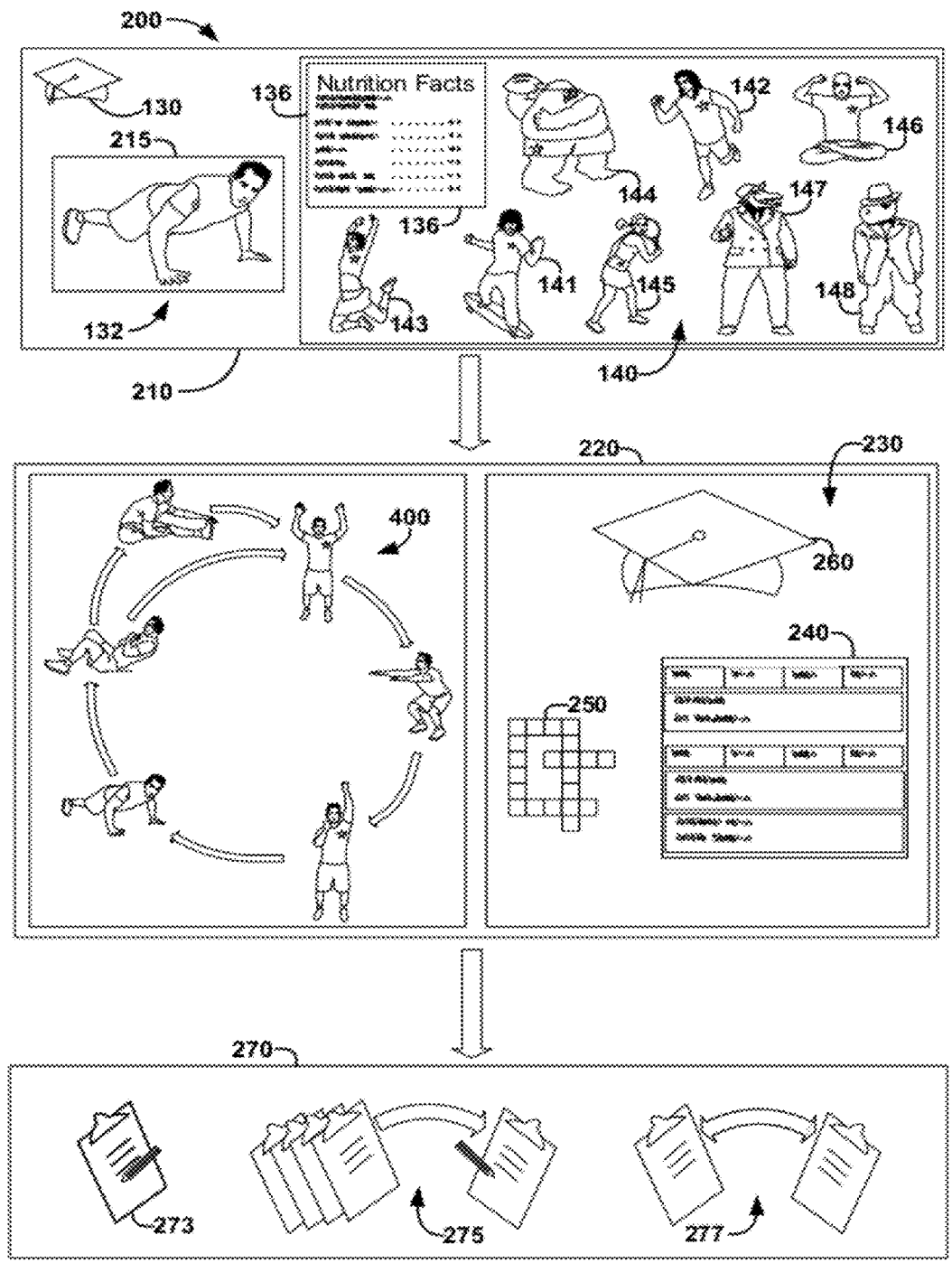
FIG. 2 shows a schematic view, illustrating at least one learning cycle of such health and fitness system, according to the preferred embodiment of FIG. 1.

FIG. 2 shows a schematic view, illustrating at least one learning cycle 200 of health and fitness program 102, according to the preferred embodiment of FIG. 1. Materials and instruction of learning cycle 200 are preferably contained in student materials 150. Learning cycle 200 preferably comprises, as shown, the steps of: learning fitness and health concepts 210; applying concepts through action 220; and recording accomplishments 270.

In step Learning Fitness and Health Concepts 210, student 821 preferably learns health and fitness education 130, as shown. By learning nutrition understanding 134 and exercise technique 132, student 821 may preferably be motivated to accomplish step Applying Concepts Through Action 220.

In step Applying Concepts Through Action 220, student 821 preferably puts into action nutrition understanding 134 and exercise technique 132 learned. Student 821 preferably employs exercise technique 132 and preferably follows exercise cycle 400 (see FIG. 4).

Further, student 821 preferably applies knowledge from health and fitness education 130 in at least one cognitive exercise 230, as shown. Cognitive exercise 230 preferably may comprise, as shown, data collection 240, alternately preferably at least one puzzle 250, alternately preferably health and fitness continuing education 260.

Puzzle 250 preferably relates to health and fitness education 130, preferably assisting student 821 preferably to develop understanding and preferably recollection of health and fitness education 130. Puzzle 250 may preferably comprise word searches, cryptograms, and crosswords. Upon reading this specification, those skilled in the art will now appreciate that, under appropriate circumstances, considering such issues as future cognitive puzzles, cost, etc., other puzzles, such as, for example, word fill-ins, scrambled words, etc., may suffice.

Health and fitness continuing education 260 preferably reinforces information about nutritional element 138 and preferably provides questions preferably designed to test comprehension of nutritional element 138. Educational stories relating to nutrition-associated character 140 may preferably be employed to expound at least one application of health and fitness education 130 in varying situations. Comprehension questions preferably require information implied, but not directly quoted within student materials 150, preferably increasing comprehension and retention of heath and fitness education 130.

Data collection 240 preferably comprises collection of data on health and fitness habits of student 821, preferably including exercise activity and preferably nutrition consumption. Data collection 240 and analyzing data collected preferably provide opportunities to integrate learning cycle 200 into science 128 using the scientific method. Data collection 240 also preferably provides a framework of accountability in accomplishing step Applying Concepts Through Action 220, preferably providing data to measure progress of student 821.

In step Recording Accomplishments 270, student 821 preferably keeps, as shown, at least one daily record 273 (refer to FIG. 5 for content details) and preferably at least one weekly record 275 (refer to FIG. 6 for content details), as well as, preferably makes comparative record 277 (refer to FIG. 7 for content details) to assist in tracking the accomplishments of student 821. Daily record 273, weekly record 275, and comparative record 277 preferably assist in data collection 240.

Figure 3:
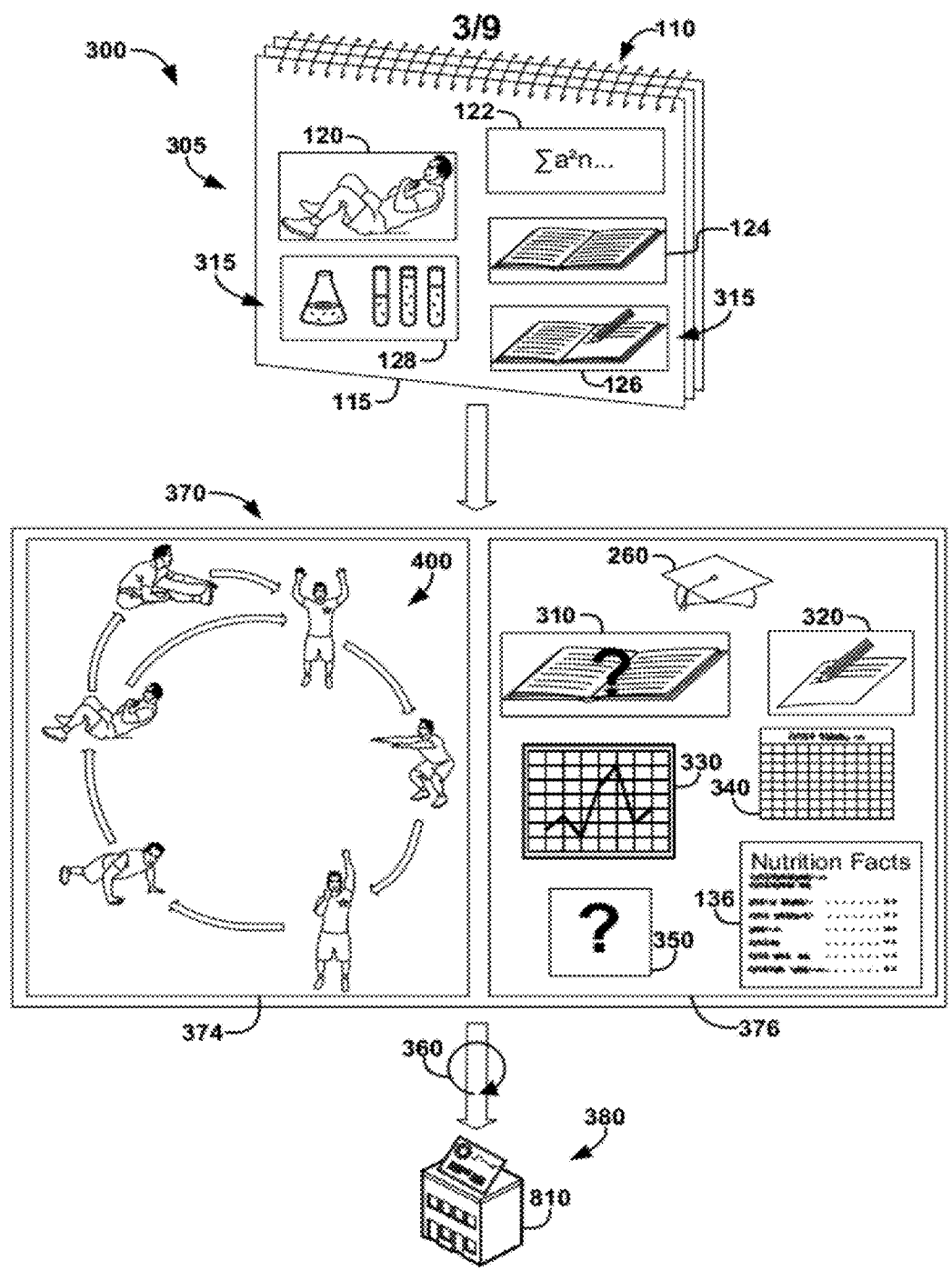
FIG. 3 shows a schematic view, illustrating at least one teaching cycle of such health and fitness system, according to the preferred embodiment of FIG. 2.

FIG. 3 shows a schematic view, illustrating at least one teaching cycle 300 of health and fitness program 102, according to the preferred embodiment of FIG. 1. Materials required for implementation instruction of teaching cycle 300 are preferably contained in curriculum instruction manual 115. Teaching cycle 300 preferably comprises, as shown, the steps of: Integrate Learning 305; Make Assignments 370; Give Feedback 380.

In step Integrate Learning 305, integrated curriculum 110 is preferably provided in curriculum instruction manual 115, as shown. Curriculum instruction manual 115 preferably provides detailed lesson plans 315 preferably relating to mathematics 122, preferably reading 124, preferably writing 126, preferably science 128, and preferably physical education 120, as shown. Lesson plans 315 are preferably divided into classroom activities 376 and physical activities 374, as shown. Physical activities 374 preferably comprise physical education 120, while classroom activities 376 preferably comprise mathematics 122, reading 124, writing 126, and science 128.

In step Make Assignments 370, physical activities 374 and classroom activities 376 are preferably assigned, as shown, preferably using lesson plans 315. At least one assignment in physical activities 374 preferably comprises exercise cycle 400, as shown. In the first lesson of physical activities 374, exercise cycle 400 is preferably explained to student 821 and exercise technique 132 is preferably taught to student 821; subsequent lessons preferably focus on performing exercise cycle 400 (at least herein embodying wherein use of such education materials to benefit of such children promotes at least one exercise cycle) and preferably incrementally increase length of exercise time.

Assignments in classroom activities 376 preferably comprise, as shown, health and fitness continuing education 260, reading assignments 310, writing assignments 320, data collecting assignments 340, data analysis assignments 330, quizzes 350, and assignments relating to food-product nutritional information 136.

Classroom activities 376 preferably interrelate with one another. Health and fitness continuing education 260 preferably incorporates reading assignments 310 and writing assignments 320 in particular, effectively integrating both reading 124 and writing 126. Reading assignments 310 preferably focus on topics within health and fitness continuing education 260. Further, reading assignments 310 are preferably assessed using comprehension questions. Writing assignments 320 preferably comprise essay writing and letter writing, preferably relating to topics within health and fitness continuing education 260.

Data collecting assignments 340 and data analysis assignments 330 preferably incorporate scientific method practices to effectively integrate science 128. Data collecting assignments 340 preferably incorporate organized data collection using tables and lists preferably in preparation for data analysis assignments 330. Data analysis assignments 330 preferably incorporate graphing analysis of data, compiling multiple sets of data, and making connections between causes and effects.

In addition, data analysis assignments 330 preferably integrate mathematics 122 in an applied setting. By applying mathematics 122 in data analysis assignments 330, comprehension of mathematics by student 821 preferably increases from connecting mathematics to real-world use. In step Give Feedback 380, feedback 360 on health and fitness program 102 may preferably be given to at least one health and fitness system originator 810, as shown. Feedback 360 may preferably be used preferably to improve health and fitness system 100. Feedback 360 may preferably comprise comments from student 821, at least one family 835, and/or at least one instructor 829.

Figure 4A:
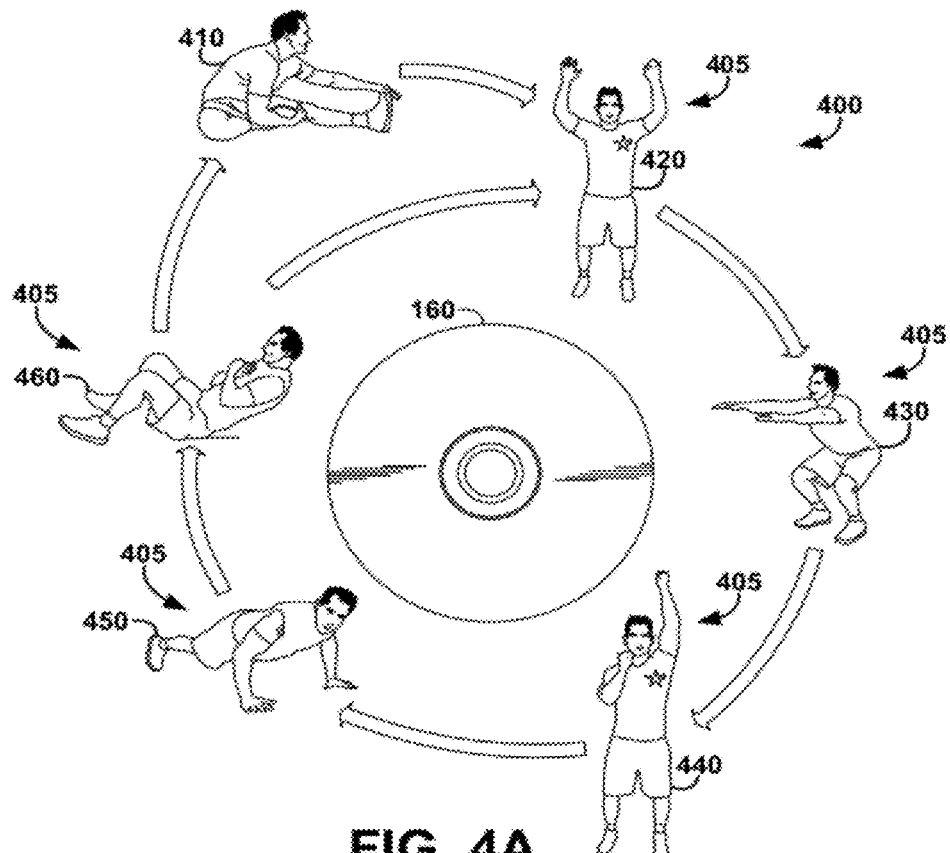
FIG. 4A shows a schematic view, illustrating at least one exercise cycle of such health and fitness system, according to the preferred embodiment of FIG. 3.

FIG. 4A shows a schematic view, illustrating exercise cycle 400 of health and fitness program 102, according to the preferred embodiment of FIG. 1. Employing exercise technique 132 in exercise cycle 400 preferably comprises using multiple exercises 405 preferably conducted in cyclical fashion.

Exercise cycle 400 preferably begins with at least one stretching routine 410, as shown. Beginning exercise cycle 400 with at least one stretching routine 410 preferably warms up muscles and preferably aids in preventing injury during performance of exercise cycle 400. Exercise cycle 400 then preferably utilizes exercises 405, in series, as shown, preferably comprising jumping jacks 420, chicken squats 430, uprights 440, push-ups 450, and sit-ups 460. Upon reading this specification, those skilled in the art will now appreciate that, under appropriate circumstances, considering such issues as future exercise methods, physical abilities of students, physical goals, etc., other exercises, such as, for example, crunches, jogging in place, arm rotations, etc., may suffice.

Each exercise 405 is preferably performed, according to exercise technique 132, for between about 20 seconds and about two minutes. Exercises 405 that are more strenuous are preferably performed for less time than exercises 405 that are less strenuous. By performing exercises 405 in cyclical fashion with varying times, rest may preferably be obtained between repetitions of exercises 405 that are more strenuous, preferably maintaining stamina and interest of student 821, preferably allowing student 821 to complete more exercises 405.

Exercise times of health and fitness program 102 are shorter to begin with and incrementally increase during the course of health and fitness program 102. This preferably builds the stamina and strength of student 821 over the course of health and fitness program 102 by providing reasonable goals to promote success of student 821 with less risk of injury and/or student perceived failure.

Jumping jacks 420, according to exercise technique 132, are preferably begun standing upright on the balls of the feet, with knees slightly bent and arms raised to shoulder height. Rhythmic jumping preferably commences in conjunction with outward and inward motions of the feet, as well as, upward and downward motions of the arms. Outward and upward motions preferably coincide simultaneously with one jump while inward and downward motions preferably coincide simultaneously with a subsequent jump. In the beginning, repetitions continue preferably for about 30 seconds. Repetitions preferably incrementally increase, preferably for up to about 60 seconds over the course of about eight weeks.

Chicken squats 430, according to exercise technique 132, are preferably begun standing with legs shoulder width apart, knees slightly bent, and arms at the sides of the waist with elbows bent. Then, while slowly squatting, the arms are preferably extended directly to the front, preferably while breathing in; breathing out preferably accompanies a return to the beginning position (standing with legs shoulder width apart, knees slightly bent, and arms at the sides of the waist with elbows bent). Repetitions preferably continue preferably for about 20 seconds, in the beginning, preferably incrementing up to about 50 seconds preferably over the course of about eight weeks.

Uprights 440, according to exercise technique 132, are preferably performed jogging in place while moving arms up and down over the head. Arm movement preferably ranges from where the hand is at the chin to fully extended directly above the head; the arm fully extended preferably coincides with the foot raised from the floor. Repetitions preferably continue preferably for about 40 seconds, preferably increasing to about 80 seconds preferably over the course of about eight weeks.

Push-ups 450, according to exercise technique 132, are preferably performed with hands and feet shoulder width apart. A push-up is preferably performed by lowering the chest near to the ground, while breathing in, and returning to a position with elbows slightly bent, while breathing out. Repetitions preferably continue preferably for about 10 seconds, preferably increasing incrementally to about 30 seconds preferably over the course of about eight weeks.

Sit-ups 460, according to exercise technique 132, are preferably performed lying down with knees bent with feet separated and the small of the back flat against the ground. The stomach muscles are preferably used to lift the shoulders off the ground, preferably while leaving the small of the back flat against the ground, and then preferably used to lower the shoulders back to the ground. Lifting is preferably performed while breathing out and lowering is preferably performed while breathing in. Repetitions preferably continue preferably for about 15 seconds, preferably increasing to about 35 seconds preferably over the course of about eight weeks.

Exercise cycle 400, according to exercise technique 132, preferably rotates through each exercise 405 to complete one cycle. Student 821 preferably completes multiple cycles before completing stretching routine 410 again, preferably about three cycles to begin with, preferably incrementing to about six cycles over the course of about eight weeks. Stretching routine 410 at the end of exercise cycle 400 preferably allows cool down time for muscles and preferably aids in preventing cramping and injury.

Upon reading this specification, those skilled in the art will now appreciate that, under appropriate circumstances, considering such issues as student capabilities, medical understanding, physical fitness requirements, etc., other exercise techniques, such as, for example, heart rate maintenance, extended exercise routines, targeted physical therapy, etc., may suffice.

Exercise cycle 400 is preferably detailed on multimedia disc 160 (at least embodying herein providing such at least one exercise cycle on at least one multimedia disc) preferably capable of providing real-time instruction, timing, and music in at least one multimedia presentation 470. Upon reading this specification, those skilled in the art will now appreciate that, under appropriate circumstances, considering such issues as available media formats, costs, etc., other methods of detailing exercise cycle, such as, for example, computer files, electronic music files, videotape, etc., may suffice.

Figure 4B:
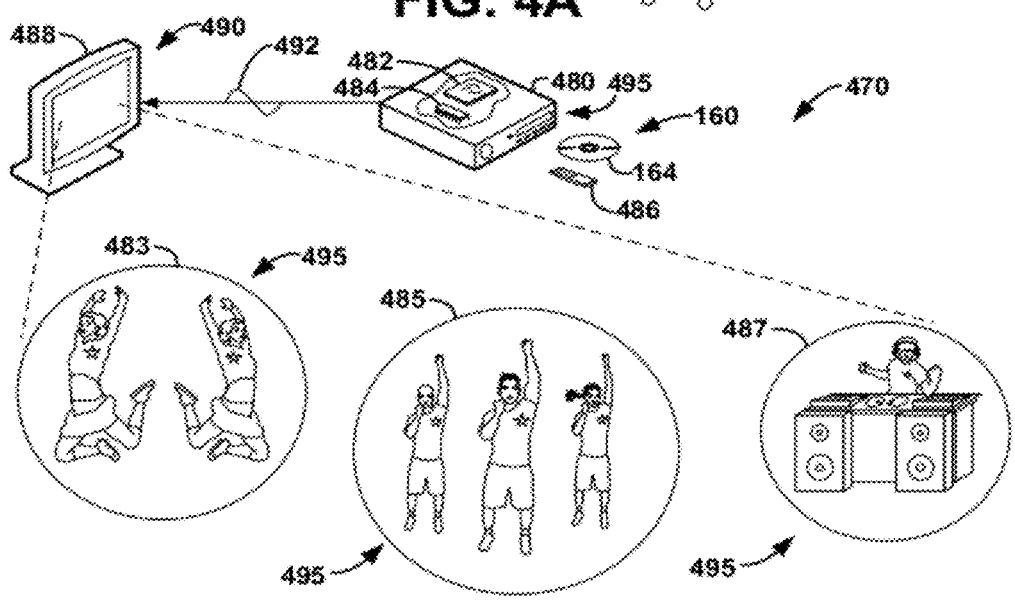
FIG. 4B shows a schematic view, illustrating at least one multimedia presentation of such at least one exercise cycle, according to the preferred embodiment of FIG. 4A.

FIG. 4B shows a schematic view, illustrating multimedia presentation 470 of exercise cycle 400, according to the preferred embodiment of FIG. 4A. Multimedia disc 160 is preferably played in at least one multimedia player 495, as shown. Multimedia player 495 preferably comprises at least one processor 482 preferably designed to convert information from multimedia disc 160 to at least one audio/video output signal 492. Multimedia player 495 preferably further comprise at least one memory chip 484, and preferably at least one input device, preferably at least one remote control 486, as shown. When multimedia disc 160 comprises DVD 164, multimedia player 495 preferably comprises at least one DVD player 480, as shown.

Audio/video output signal 492 is preferably interpreted by at least one output device 490, preferably at least one video screen 488, as shown. Video screen 488 preferably displays at least one element 496 of exercise cycle 400 contained on multimedia disc 160, as shown. Upon reading this specification, those skilled in the art will now appreciate that, under appropriate circumstances, considering such issues as media type, cost, etc., other multimedia players, such as, for example, CD players, MP3 players, tape players, etc., may suffice.

Element 496 of exercise cycle 400 may preferably comprise at least one dancer 483, music 487, and at least one demonstrator 485, as shown. Demonstrator 485 preferably provides visual instruction on proper performance of exercise 405. Music 487 preferably provides entertainment and rhythm by which to perform exercises 405. Dancer 483 preferably provides entertainment value to exercise cycle 400. Using multimedia disc 160 preferably provides simplified instruction, exercise rhythm, and timing of repetitions. Upon reading this specification, those skilled in the art will now appreciate that, under appropriate circumstances, considering such issues as cost, future technologies, etc., other presentation methods, such as, for example, live concerts, television broadcasts, interactive game console play, holographic projection, etc., may suffice.

Figure 5:
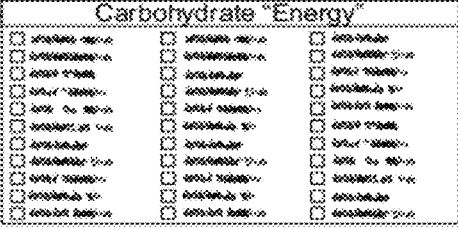
FIG. 5 shows a schematic view, illustrating at least one daily tracking form, according to the preferred embodiment of FIG. 3.

FIG. 5 shows a schematic view, illustrating at least one daily tracking form 500, according to the preferred embodiment of FIG. 1. Daily tracking form 500 is preferably used in keeping daily record 273. Daily tracking form preferably comprises, as shown, at least one day-indicator 510, preferably at least one data type indicator 520, preferably at least one food list 530, preferably at least one self-examination prompt 560, and preferably at least one exercise tracking area 570. Daily tracking form 500 is preferably designed to allow data collection on a daily basis and to preferably assist in associating food consumption and exercise with physical well-being.

Data type indicator 520 preferably indicates the type of data being tracked, preferably food consumption, alternately preferably water consumption, alternately preferably exercises performed, and alternately preferably physical well-being. Upon reading this specification, those skilled in the art will now appreciate that, under appropriate circumstances, considering such issues as goals, costs, physical capabilities, etc., other types of data, such as, for example, physical activities, sleep, consumption schedule, etc., may suffice.

Food list 530 may preferably comprise carbohydrate food list 532, alternately preferably protein food list 534, alternately preferably vitamin and mineral food list 536, as shown. Each food list 530 preferably comprises at least one food 540 and preferably at least one data input field 542, as shown. Data input field 542 preferably comprises at least one checkbox 550, alternately preferably at least one count box 552, as shown. Data input field 542 preferably allows the indication of the consumption of food 540. Additionally, when data input field comprises count box 552, data input field 542 preferably allows the indication of how much of food 540 is consumed. Each food list 530 is preferably associated with nutrition-associated character 140.

Self-examination prompt 560, as shown, preferably provides at least one area to indicate well-being of student 821. Exercise tracking area 570, as shown, preferably allows the tracking of exercises 405. Daily tracking form 500 is preferably designed to track data as activities are being done for later examination in weekly record 275.

Figure 6:
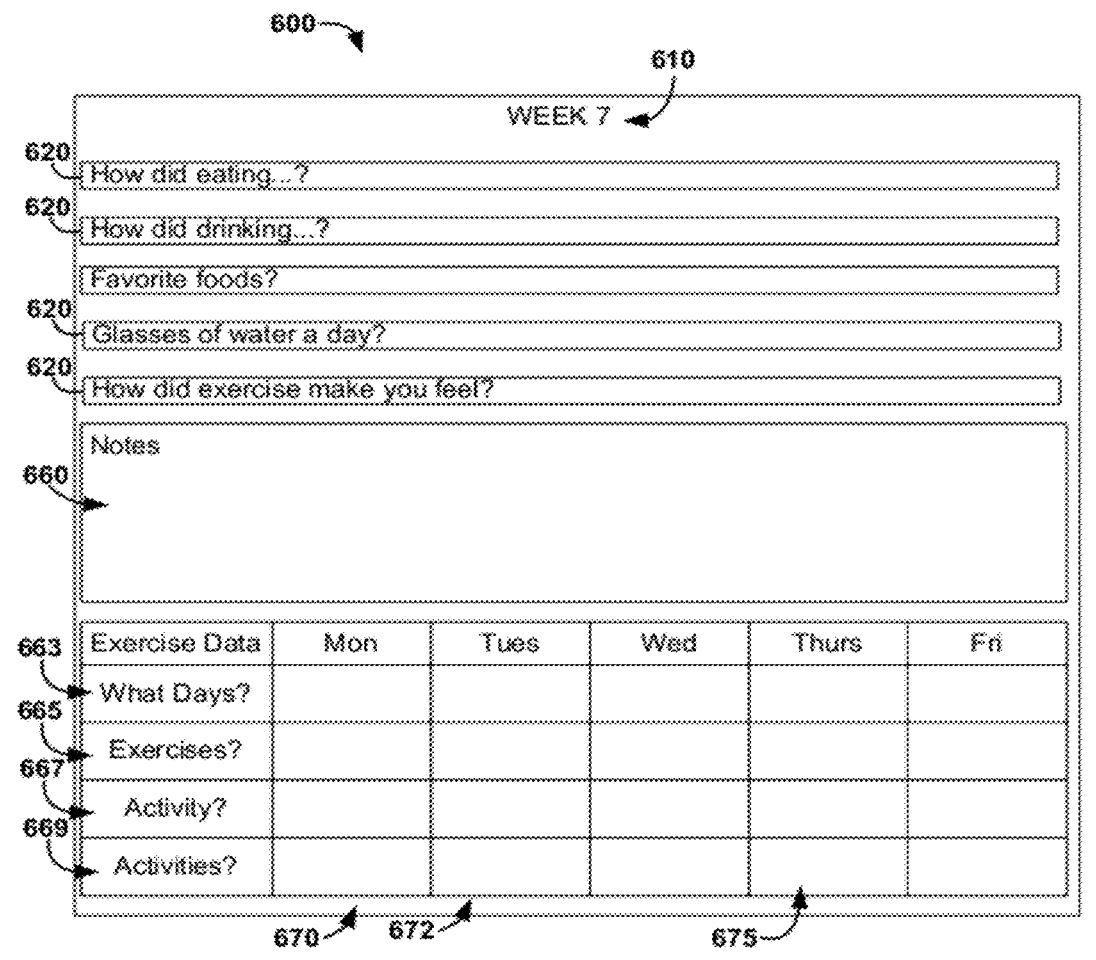

FIG. 6 shows a schematic view, illustrating at least one weekly tracking form 600, according to the preferred embodiment of FIG. 1. Weekly tracking form 600 is preferably used in compiling and tracking of weekly record 275 from daily record 273. Weekly tracking form 600 preferably comprises at least one week-indicator 610, preferably at least one data analysis prompt 620, preferably at least one exercise data log 670 and preferably at least one notes area 660, as shown.

Data analysis prompt 620 preferably asks student 821 to associate consumption habits with daily-assessed well-being. Data analysis prompt 620 preferably also asks student 821 to associate exercise patterns with daily-assessed well-being. Data analysis prompt 620 preferably also requests at least one calculated average of consumption of food 540, preferably water.

Exercise data log 670 preferably comprises at least one table 672 preferably comprising at least one data entry cell 675, as shown. Data entered into exercise data log 670 preferably comprises the days of exercise 663, exercises performed 665, other physical activities performed 667, as well as, physical activity counts 669, as shown.

Figure 7:
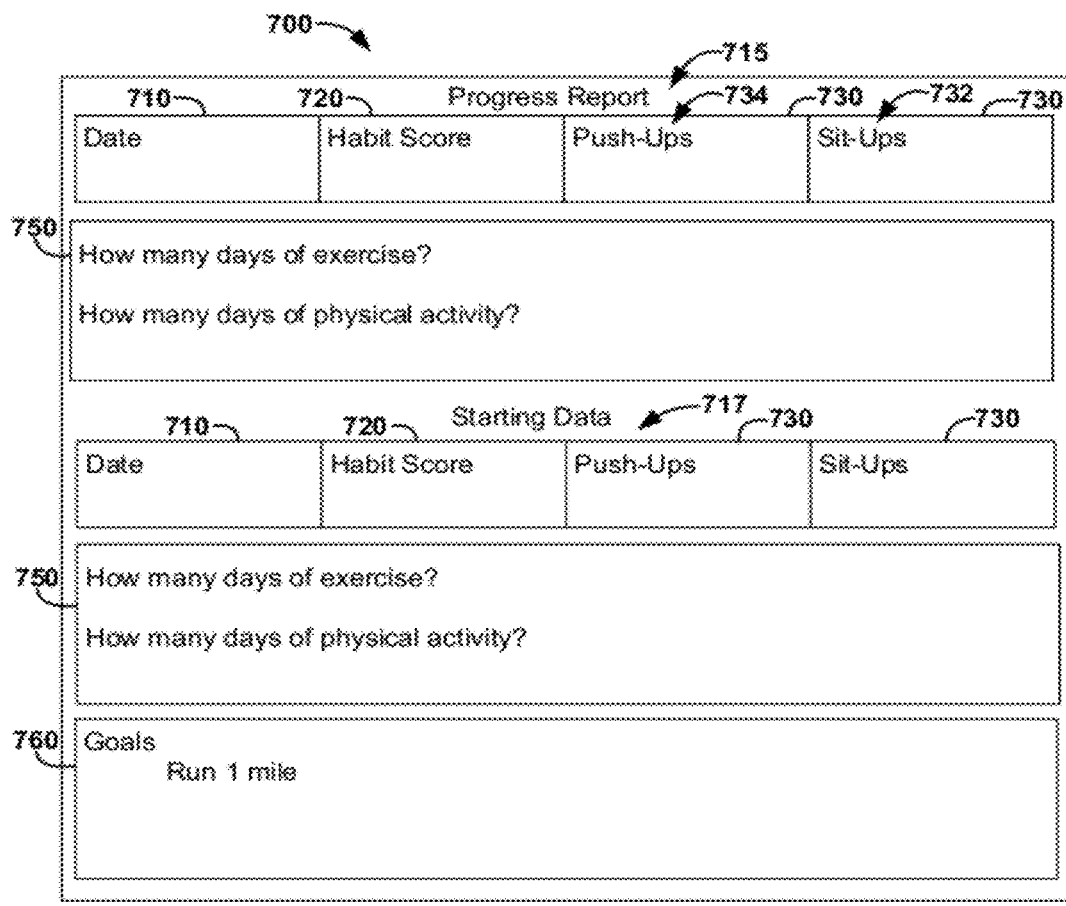
FIG. 7 shows a schematic view, illustrating at least one comparative progress form, according to the preferred embodiment of FIG. 3.

FIG. 7 shows a schematic view, illustrating at least one comparative progress form 700, according to the preferred embodiment of FIG. 1. Comparative progress form 700 preferably used in making comparative record 277. Comparative progress form 700 preferably provides an opportunity for student 821 to compare quantitative assessments 755 of at least one current assessment 715 and at least one prior assessment 717, as shown. Comparative progress form 700 preferably additionally provides place for at least one goal 760, preferably to assess progress of student 821 toward goal 760, as shown.

Quantitative assessments 755 preferably comprise the date of assessment 710, preferably at least one habit score 720, preferably at least one exercise count score 730, and preferably at least one count of days 750 for physical activities and exercising, as shown. Upon reading this specification, those skilled in the art will now appreciate that, under appropriate circumstances, considering such issues as exercise methods, assessment methods, etc., other areas of quantitative assessment, such as, for example, checklists, goal accomplishments, physical assessments, etc., may suffice.

Exercise count score 730 preferably comprises at least one count of push-ups 734 and preferably at least one count of sit-ups 732, as shown. Upon reading this specification, those skilled in the art will now appreciate that, under appropriate circumstances, considering such issues as exercise methods, available data, etc., other exercise count scores, such as, for example, pull-ups, running times, flexibility, etc., may suffice.

Habit score 720 preferably derives from at least one series of questions ascertaining habits of student 821 preferably regarding nutritional health and fitness. Habit score 720 preferably uses identical questions for both current assessment 715 and prior assessment 717. Upon reading this specification, those skilled in the art will now appreciate that, under appropriate circumstances, considering such issues as costs, available nutritional health and fitness assessments, etc., other scores regarding nutritional health and fitness, such as, for example, medical examinations, clinical examinations, self-examinations, etc., may suffice.

FIG. 8 shows a schematic view, illustrating at least one health and fitness method 800, according to the preferred embodiment of FIG. 1. Health and fitness method 800 preferably comprises health and fitness system originator 810 providing, as shown, health and fitness program 102 to at least one school system 820, alternately preferably to at least one home school 830. Health and fitness method 800 preferably further comprises health and fitness system originator 810 receiving support from at least one sponsor 840, alternately preferably at least one partner 850, as shown (this arrangement at least embodying herein obtaining at least one sponsor). Health and fitness system originator 810 preferably promotes health and fitness program 102 as a benefit to student 821 (this arrangement at least embodying herein promoting use of such education materials to benefit of such children).

Health and fitness system originator 810 preferably operates at least one website 895, as shown, preferably promoting health and fitness program 102 and preferably providing access for school district 823 and home school 830 to obtain health and fitness program 102 (this arrangement at least embodying herein at least one educational materials promoter structured and arranged to promote use of such education materials to benefit of such children). Student materials 150 and curriculum instruction manual 115 are preferably available, preferably for purchase, through website 895 (at least embodying herein providing education materials; at least embodying herein at least one web site providing such educational materials; and at least embodying herein providing at least one web site to obtain such educational materials). Student 821 preferably receives student materials 150 while participating in health and fitness program 102, as shown.

Instructor 829, instructing at least one class 827, preferably uses curriculum instruction manual 115. Student materials 150 and curriculum instruction manual 115 are preferably obtained by school district 823, alternately preferably by school 825, alternately preferably by class 827.

Health and fitness system originator 810 preferably promotes motivational character 180 and nutrition-associated character 140 (this arrangement at least embodying herein marketing such at least one cartoon character). Additionally, health and fitness system originator 810 may preferably provide at least one personal appearance 815 (at least embodying herein providing at least one personal appearance of such at least one cartoon character; and at least embodying herein at least one personal appearance of such at least one cartoon character) of motivational character 180, as shown, and nutrition-associated character 140. Personal appearance 815 preferably aids in motivating student 821 in participating in health and fitness system 100.

Additionally, health and fitness system originator 810 preferably promotes competition 880 (at least embodying herein at least one competition structured and arranged to promote participatory interest of children), preferably increasing interest of student 821 in participating (this arrangement at least embodying herein promoting at least one competition structured and arranged to promote participatory interest of children). Health and fitness system originator 810 preferably obtains and preferably distributes prizes 860, preferably to winners of competition 880 and preferably to participants of health and fitness program 102 (this arrangement at least embodying herein providing at least one prize related to such at least one competition).

Sponsor 840 preferably comprises at least one medical establishment 843, alternately preferably at least one insurance company 845, alternately preferably at least one corporate sponsor 847, as shown. Sponsor 840 preferably provides funding 892 to health and fitness system originator 810 preferably to finance operations, as shown. Sponsor 840 alternately preferably directly sponsors competition 880, as shown. Sponsor 840 alternately preferably provides prize 860 (at least embodying herein at least one prize related to such at least one competition) for competition 880, as shown.

Sponsor 840 preferably receives, in exchange for sponsorship, name recognition advertising associated with health and fitness program 102. Sponsor 840 preferably also receives at least one increase in patronage, alternately preferably at least one decrease in operating costs. Corporate sponsor 847 may preferably receive preferably through use of products as prizes 860 and preferably through additional name recognition advertising increased patronage from participants of health and fitness program 102. Insurance company 845 preferably receives at least one decrease in overhead costs associated with insurance claims due to medical needs of participants of health and fitness program 102. Medical establishment 843 preferably receives increased patronage and preferably increased donations from name recognition by participants of health and fitness program 102.

Partner 850 preferably provides direct advertisement, in at least one retail environment, of health and fitness system 100 preferably in exchange for directed traffic of customers from health and fitness system 100 to partner 850, as shown. Partner 850 may also preferably choose to provide discounts to participants of health and fitness system 100 to increase incentive of participants to purchase goods from partner 850.

Figure 9:
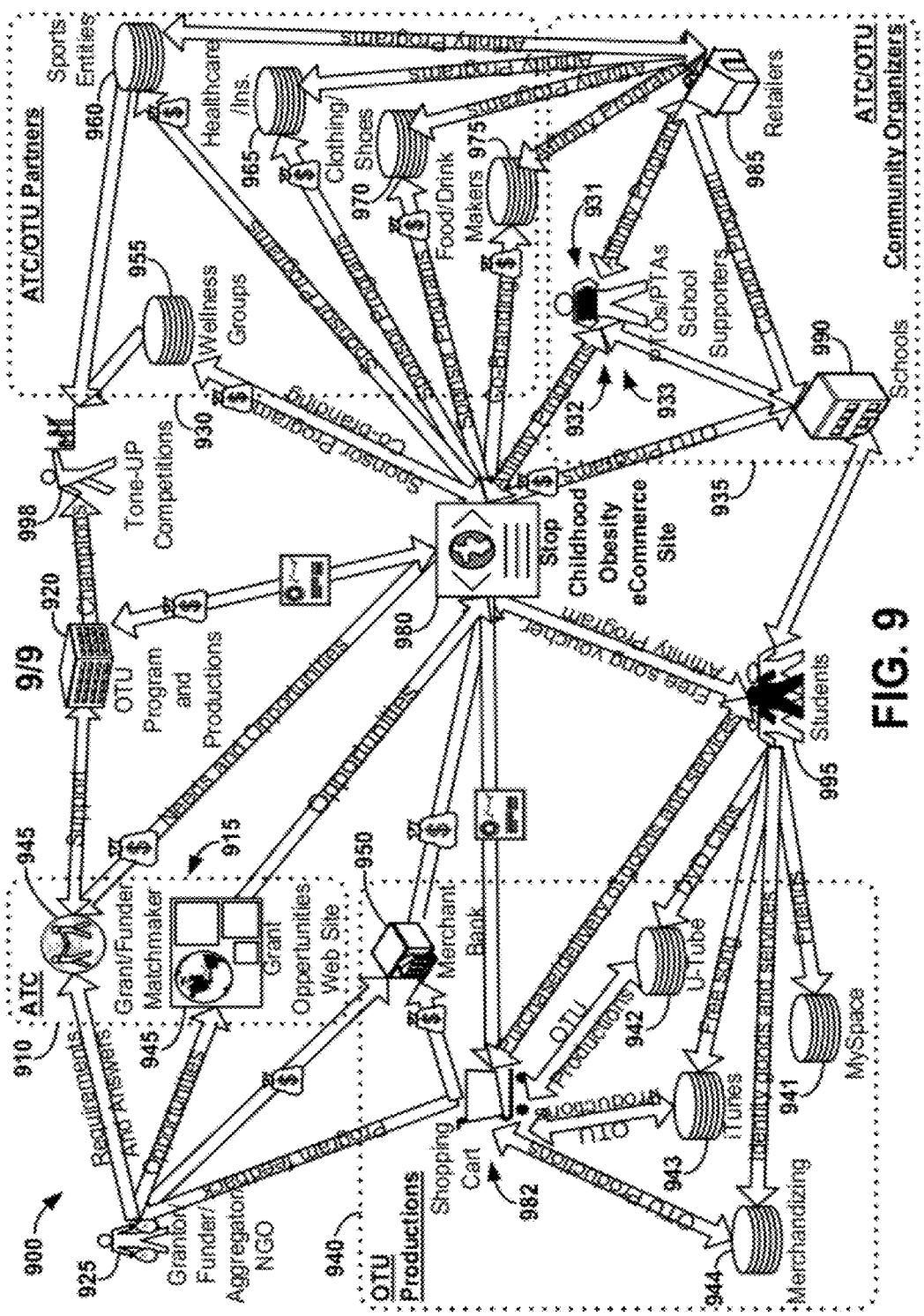
FIG. 9 shows a schematic view, illustration an alternately preferred health and fitness method, according to the preferred embodiment of FIG. 4B.

FIG. 9 shows a schematic view, illustrating an alternately preferred health and fitness method, according to the preferred embodiment of FIG. 4B. Childhood obesity prevention and mitigation method 900 preferably comprises at least one fundraising entity 915 and preferably at least one health and fitness operations entity 920.

At least one non-profit entity 910, shown as Accept a Challenge (ATC), comprises fundraising entity 915 for health and fitness program 102, shown as Operation Tone Up (OTU), which comprises health and fitness operations entity 920 with a mission of substantially reducing childhood obesity. Childhood obesity prevention and mitigation method 900 preferably has as a mission the funding, preferably operating and implementing a series of anti-obesity programs, including health and fitness program 102, that focus preferably specifically on children.

Childhood obesity prevention and mitigation method 900 preferably comprises at least one scalable means for monetizing fund flows from multiple funding sources while deploying health and fitness program 102, by multiple interactions with ATC/OTU funders 925, ATC/OTU partners 930, ATC/OTU community organizers 935, and OTU productions 940. At the core of the scalability of childhood obesity prevention and mitigation method 900 is preferably the deployment of related activities via a scalable electronic means such as the Internet.

ATC/OTU funders 925 preferably comprise civic-minded grantors, funders, aggregators of funds, and non-government organizations (NGOs), and government entities. Upon reading this specification, those skilled in the art will now appreciate that, under appropriate circumstances, considering such issues as cost, availability of funds, etc., other ATC/OUT funders, such as, for example, religious organizations, individuals, student organizations, etc., may suffice.

Fundraising entity 915 preferably primarily interfaces with ATC/OTU funders 925 via electronic means, preferably comprising at least one website 945 which displays grant opportunities and electronically enables matching of grant funders with ATC/OTU grant opportunities. Proceeds from ATC/OTU partners 930 preferably are provided to fundraising entity 915 electronically via a merchant banking entity 950 and are preferably electronically assigned to specific ATC/OTU childhood obesity prevention and mitigation activities—preferably as electronically selected by ATC/OTU funders 925. Statuses of subsequent grant activities are preferably provided back to ATC/OTU funders 925 via electronic means. Thus, this process is preferably scalable for potentially a worldwide implement of childhood obesity prevention and mitigation method 900.

ATC/OTU partners 930 comprise multiple entities that share a common characteristic of being stakeholders in the encouragement of children to adopt more healthy lifestyles. ATC/OTU partners 930 preferably include wellness groups 955, sports entities 960, healthcare and insurance entities 965, clothing and shoe related-entities 970, and food and drink related-entities 975. Upon reading this specification, those skilled in the art will now appreciate that, under appropriate circumstances, considering such issues as, interest, cost, etc., other ATC/OUT partners, such as, for example, physical activity electronic game manufacturers, political entities, community organizations, etc., may suffice.

Fitness operations entity 920 preferably interfaces with ATC/OTU partners 930 via at least one e-commerce web-based site 980. Further, e-commerce web-based site 980 preferably allows and promotes interaction between and among ATC/OTU partners 930 as well as preferably between fitness operations entity 920 and ATC/OTU partners 930. Also, e-commerce web-based site 980 preferably allows and promotes interaction between and among ATC/OTU partners 930 and their respective retailers (local retailers 985), which preferably are situated in neighborhoods where children live and go to school. Upon reading this specification, those skilled in the art, will now appreciate that, under appropriate circumstances, considering such issues as cost, future technologies, etc., other electronic communications, such as, for example, email, instant messaging, non-e-commerce based websites, etc., may suffice.

Childhood obesity prevention and mitigation method 900 preferably leverages interactions of ATC/OTU partners 930 with their respective local retailers 985, and interactions of the local retailers 985 with local schools 990, such that students 995 in local schools 990 are more likely to patronize the local retailers 985. In return, local retailers 985 preferably provide grants and fundraising for deploying health and fitness program 102 in local schools 990. Childhood obesity prevention and mitigation business method 900 preferably coordinates the multiple neighborhood-level interactions between local retailers 985 and local schools 990 with ATC/OTU partners 930 such that similar implementations of health and fitness program 102 can be deployed across many such neighborhoods, thus preferably allowing health and fitness program 102 to be scaled throughout substantial populations.

ATC/OTU community organizers 935 comprise parent teacher organizations 931, parent teacher associations 932, and other school supporters 933. Childhood obesity prevention and mitigation method 900 preferably provides ATC/OTU community organizers 935 with affinity programs that encourage interaction and funds flow between local retailers 985 and local schools 990. Childhood obesity prevention and mitigation method 900 preferably further provides affinity programs that are coordinated with ATC/OTU partners 930 via e-commerce web-based site 980. The affinity programs are preferably architected and monitored by fitness operations entity 920 via e-commerce web-based site 980. Still further, childhood obesity prevention and mitigation method 900 preferably provides co-branding and related sponsor programs that are coordinated with ATC/OTU partners 930 via e-commerce web-based site 980. The co-branding and related sponsor programs are preferably also architected and monitored by fitness operations entity 920 via e-commerce web-based site 980.

OTU productions 940 comprise such social interaction sites as MySpace 941, U-Tube 942, iTunes 943 as well as at least one OTU productions merchandizing website 944. Such social interaction sites, particularly those sites that allow for user interactions within a safe environment for children, are useful for creating interest in health and fitness program 102. Incentive and related affinity programs of OTU productions 940 are preferably deployed in a scalable fashion to students 995 via e-commerce website infrastructure 982, merchant banking infrastructure 950 and related network infrastructure.

An example affinity program is one that is built around the OTU musical properties. Such affinity program, for example, provides a free OTU song to each student 995 that opens a MySpace account that is affiliated with e-commerce web-based site 980. Similarly, a free OTU song, ring-tone, cell phone skin, etc. is given to students 995 that socially interact with other students 995 or teachers in a fashion that promotes the ATC/OTU mission of reducing childhood obesity.

Additionally, such affinity programs drive student traffic to OTC merchandizing website 944 where students 995 and their families can electronically purchase OTU related merchandize. The OTU merchandize preferably features motivational character 180 and/or nutrition-associated character 140, representing the various nutrients, which are taught in health and fitness program 102, thus, providing reinforcement of health and fitness program 102 as students 995 continue to their normal everyday living. Upon reading this specification, those skilled in the art will now appreciate that, under appropriate circumstances, considering such issues as cost, future technologies, etc., other merchandize features, such as, for example, motivational phrases, logos, contests, websites, etc., may suffice.

OTU productions 940 also preferably provide the creative force and support that drives childhood obesity prevention and mitigation method 900. OTU productions 940 preferably organizes a series of competitions 998 of students 995 representing two or more of local schools 990, or groupings of local schools 990, such as representing metropolitan areas, or states, etc. Competitions 998 are preferably intended to reward students 995 who participate and, more broadly, to call attention to fighting childhood obesity. Childhood obesity prevention and mitigation method 900 preferably also calls for OTU productions 940 to generate publicity for competitions 998 from both traditional media and via the Internet. In return for the use of nutrition-associated character 140, stories, and related OTU artifacts, to ATC/OTU funders 925, ATC/OTU partners 930, ATC/OTU community organizers 935, childhood obesity prevention and mitigation method 900 preferably provides for charging of OTU productions 940 for the use and exposure of its intellectual property as well as related services.

Although applicant has described applicant's preferred embodiments of this invention, it will be understood that the broadest scope of this invention includes modifications such as diverse shapes, sizes, and materials. Such scope is limited only by the below claims as read in connection with the above specification. Further, many other advantages of applicant's invention will be apparent to those skilled in the art from the above descriptions and the below claims.

What is claimed is:

1. An article of manufacture including a non-transitory, tangible, computer readable storage medium having instructions stored thereon that, in response to execution by a computer-based system for educating a child, cause the computer-based system to perform operations comprising displaying, by the computer-based system, a cartoon character to promote educational interest in the child;

displaying, by the computer-based system and in association with the cartoon character, educational materials to teach a child about a relationship between a nutrient that is not listed on a nutrition label and the child's health;

displaying, by the computer-based system, educational materials to teach the child bow to calculate a value for the nutrient that is not listed on the nutrition label based upon two nutrients that are listed on the nutrition label;

displaying, by the computer-based system, the nutrition label;

receiving, by the computer-based system, a calculation of the value for the nutrient that is not listed on the nutrition label that is performed by the child based upon the nutrition label;

instructing, by the computer-based system, the child to consume a food that contains the two nutrients that are listed on the nutrition label;

instructing, by the computer-based system, the child to perform an exercise regimen; and receiving, by the computer-based system, feedback from the child that describes the child's ability to perform the exercise regimen in association with the two nutrients that are listed on the nutrition label.

2. The article according to claim 1 further comprising displaying, by the computer-based system, at least one competition to promote participatory interest in the child.

3. The article according to claim 1 further comprising at least one prize related to at least one competition.

4. The article according to claim 3 wherein the at least one prize comprises at least one monetary prize.

5. The article according to claim 3 wherein the at least one prize comprises at least one voucher.

6. The article according to claim 3 wherein the at least one prize comprises at least one hand-held electronic device.

7. The article according to claim 3 wherein the at least one prize comprises at least one computer system.

8. The article according to claim 3 wherein the at least one prize comprises at least one multimedia prize.

9. The article according to claim 2 wherein the at least one competition is sponsored by at least one sponsor.

10. The article according to claim 1 wherein the cartoon character represents at least one nutritional element.

11. The article according to claim 10 wherein the cartoon character represents at least water.

12. The article according to claim 10 wherein the cartoon character represents at least protein.

13. The article according to claim 10 wherein the cartoon character represents at least carbohydrates.

14. The article according to claim 10 wherein the cartoon character represents at least minerals.

15. The article according to claim 10 wherein the cartoon character represents at least vitamins.

16. The article according to claim 10 wherein the cartoon character represents at least fats.

17. The article according to claim 10 wherein the cartoon character represents at least sodium.

18. The article according to claim 10 wherein the cartoon character represents at least sugars.

19. The article according to claim 1 wherein the educational materials comprise at least one exercise cycle.

20. The article according to claim 19 wherein the at least one exercise cycle comprises at least one multimedia disc.

21. The article according to claim 20 wherein the at least one multimedia disc comprises at least one DVD.

22. The article according to claim 20 wherein the at least one multimedia disc comprises at least one CD.

23. The article according to claim 1 wherein the instructions are configured to be downloaded from at least one web site.

24. A method comprising:

displaying, by a computer-based system for educating a child, a cartoon character to promote educational interest in the child;

displaying, by the computer-based system and in association with the cartoon character, educational materials to teach a child about a relationship between a nutrient that is not listed on a nutrition label and the child's health;

displaying, by the computer-based system, educational materials to teach the child how to calculate a value for the nutrient that is not listed on the nutrition label based upon two nutrients that are listed on the nutrition label;

displaying, by the computer-based system, the nutrition label;

receiving, by the computer-based system, a calculation of the value for the nutrient that is not listed on the nutrition label that is performed by the child based upon the nutrition label;

instructing, by the computer-based system, the child to consume a food that contains the two nutrients that are listed on the nutrition label;

instructing, by the computer-based system, the child to perform an exercise regimen; and receiving, by the computer-based system, feedback from the child that describes the child's ability to perform the exercise regimen in association with the two nutrients that are listed on the nutrition label.

* * * * *

UNITED STATES PATENT AND TRADEMARK OFFICE
CERTIFICATE OF CORRECTION

| | | |
|---|---|---|
| PATENT NO. | : 8,267,694 B1 | |
| APPLICATION NO. | : 12/493090 | |
| DATED | : September 18, 2012 | |
| INVENTOR(S) | : Anthony J. Lamka | |

It is certified that error appears in the above-identified patent and that said Letters Patent is hereby corrected as shown below:

In Column 17 Line 67, please delete "bow" and insert therefor --how--

Signed and Sealed this
Twenty-seventh Day of November, 2012

David J. Kappos
*Director of the United States Patent and Trademark Office*